United States Patent [19]

Sahadevan

[11] 4,321,208

[45] Mar. 23, 1982

[54] PREPARATION OF DIRECTLY IODINATED STEROID HORMONES AND RELATED COMPOUNDS

[76] Inventor: Velayudhan Sahadevan, 3825 Golf Rd., Evanston, Ill. 60203

[21] Appl. No.: 727,284

[22] Filed: Sep. 27, 1976

[51] Int. Cl.$^3$ .............................. C07J 5/00; C07J 1/00
[52] U.S. Cl. .............................. 260/397.3; 260/397.4; 260/397.5; 260/397.45
[58] Field of Search ............. 260/397.3, 397.4, 397.45, 260/397.5

[56] References Cited

U.S. PATENT DOCUMENTS

| | | | |
|---|---|---|---|
| 3,933,869 | 1/1976 | Schulze | 260/397.4 |
| 3,953,431 | 4/1976 | Rutner et al. | 424/241 |
| 3,954,739 | 3/1976 | Wilkinson | 260/239.57 |
| 4,013,688 | 3/1977 | Babcock et al. | 260/397.45 |

FOREIGN PATENT DOCUMENTS 1441253  6/1976  United Kingdom ........... 260/239.55

OTHER PUBLICATIONS

Chem. Abstracts, vol. 83 (1975), Par 190024y.

*Primary Examiner*—Elbert L. Roberts
*Attorney, Agent, or Firm*—Bruce K. Thomas

[57] ABSTRACT

A process for the direct iodination of steroids and steroid hormones in the presence of hydrogen peroxide or chloramine-T is disclosed. The antigenicity and the specific receptor binding of directly iodinated estradiol 17-beta is identical to tritiated estradiol 17-beta.

16 Claims, 3 Drawing Figures

TLC OF $^{125}I$-$E_2$
FRACTION NO. 5

TLC OF $^{125}$I-E$_2$ FRACTION NO. 5

$^{125}$I-E$_2$ BINDING TO SERIAL DILUTION OF E$_2$-AS $^{125}$I-ESTRADIOL

PREPARATION OF DIRECTLY IODINATED STEROID HORMONES AND RELATED COMPOUNDS

BACKGROUND OF THE INVENTION

In order to quantify the hormone present in an assay tube, it is necessary to determine the amount of hormone bound to the antibody. A radioisotopically labelled steroid is used for this purpose and according to Niwender, G. D., Akbar, A. M., and Nett, J. M. in "Methods in Enzymology, Vol. 36, Hormone Action, Part A: Steroid Hormones", Academic Press, 1975, at pp. 16–33, it is not possible to directly radioiodinate the cyclopentanophenanthrene nucleus or its substituents. Furthermore, these authors report that, although phenolic steroids can be radioiodinated directly at the 2 and 4 positions, this seems to alter the configuration of the molecule and affects the binding to the antibody because the physical dimensions of an iodine atom approximate those of the complete phenolic A ring in the molecule.

By conjugating the steroid to a tyrosene-containing protein, for example to bovine serum albumin (BSA), it is possible to radioiodinate the protein without affecting the ability of the steroid to bind to an antibody. However, there is a distinct difference between the tyrosene-containing protein and the procedure of this invention in that herein the steroid is directly iodinated. Furthermore, the use of tyrosene-containing protein does not insure that only one steroid molecule is attached to each albumin molecule and, in fact, the steroid-to-protein ratio is at least 20:1.

To prepare one steroid per radioiodinated protein, Niwender et al uses the methyl ester of tyrosine (TME) conjugated steroid protein derivative. The phenolic tyrosine ring of this derivative is easily iodinated with $Na^{125}I$ by Chloramine T procedures of iodination of proteins. The steroid-protein-TME-$^{125}I$ thus prepared is shown to possess antigenic specificity to steroid antiserum and could be used for the radioimmunoassay procedures of estrogen.

According to G. E. Abraham and W. D. Odell, "Solid Phase Radioimmunoassay of Serum Estradiol-17 beta" in "Immunologic Methods in Steroid Determinations." Peron and Caldwell (1970), estrogen ($E_2$) may be labeled with radioisotopes emitting beta- or gamma-radiations using radioactive halogens such as $^{82}Br$, $^{125}I$ and $^{131}I$ at positions C-2 and C-4 in the phenolic ring. However, the short half-life of the halogens limits its use to a few days only. Another factor, these authors report, that almost rules out the radio-active halogens as a possible marker on the $E_2$ molecule is inherent in their physical properties, namely their highly electronegative characteristics which affect the net charge of the molecules and the radioactive halogens with the longest half-life are relatively large atoms that would interfere with the steric fitness of the antibody active cites. According to these authors, directly iodinated estradiol 17-beta at positions 2 and 4 is unable to bind the antiserum because of the interference induced by the relatively large atoms of iodine with the steric fitness of these active cites of the antibody.

It is known that the steroid synthesizing organs such as the gonads, the fetoplacental unit and the adrenal cortex utilize the same precursor substances for the synthesis of steroid hormones. Also, steroid specific receptor proteins are present in various normal tissues and in certain malignant tumors. Receptor cites for both estrogen and progesterone are usually found in hormone dependent tumors such as human breast cancer.

When tritiated estradiol is injected to patients with breast cancer, those patients responding to endocrine treatment usually concentrate more tritiated hormones in their tumor tissue than those patients who do not respond to hormonal treatment. The uptake of tritiated hormone by the tumor tissue is facilitated by the presence of specific estrogen receptor sites in such tumors. Other tumors such as endometrial carcinoma and prostate cancer are known to possess specific receptor sites for steroid hormones like estrogen, progesterone and testosterone.

SUMMARY OF THE INVENTION

This invention relates to new methods of preparation of radioactive steroid hormones. The radioactive iodine labelled estradiol-17 beta thus prepared retains both its antigenic and receptor sites specificity.

The iodinated compounds of this invention are in general prepared by dissolving the steroid in an appropriate solvent such as methanol, ethanol or toluene. Methanol is the preferred solvent. To the dissolved steroid, the radioactive or non-radioactive iodine in an alkaline solution is added and the iodination reaction is allowed to take place at room temperature. The iodinated steroid is removed from the solution by centrifugation and subsequent repeated washing with either 0.1 N HCl or water. When the amount of steroid hormone used in iodination experiments is only a few micrograms, chromatographic procedures are used for the separation of labelled hormones from the unreacted iodide. The ratio of the reactants can be varied; by increasing the ratio of iodide to the steroid concentration, radio-labelled hormone with high specific activity can be prepared.

The purity of the compound thus prepared is tested by precipitation, thin layer chromatography and by the binding affinity of the labelled estradiol 17-beta to its specific antiserum and to the naturally occurring estrogen receptor sites.

DESCRIPTION OF THE DRAWINGS

In order to establish the effectiveness of the labelled steroids of this invention prepared samples were subjected to tests whereby the results are shown graphically and wherein.

DESCRIPTION OF THE PREFERRED EMBODIMENT

Figure 1:
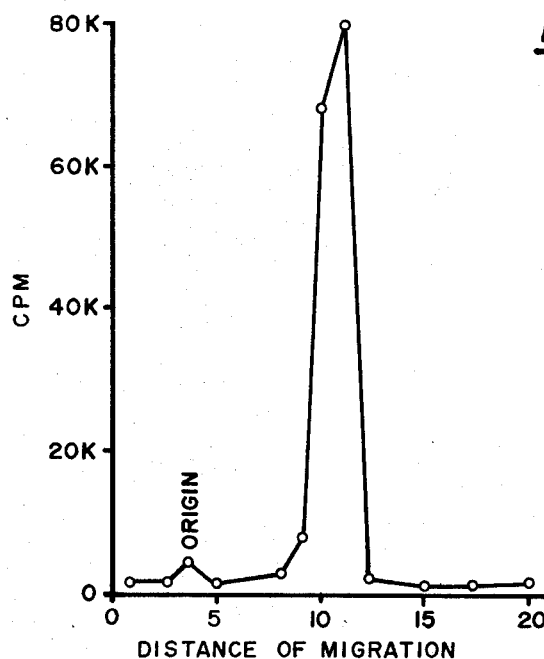
FIG. 1 is a graphical representation of the thin layer chromatogram wherein the abscissa is the distance of migration; and the ordinate is the count per minute per one cm. of chromatogram.

Example I—Iodination of Estradiol-17 beta by Hydrogen Peroxide:

Estradiol-17 beta at varying concentration ranging from 0.2724–2.724 mg. was dissolved in methanol at a volume of 10–100 lambda and allowed to react with radioactive iodide $^{125}$I as sodium iodide at a concentration varying from 10 microCurie to 1 mCi in 10 lambda of 0.0005 N KOH or NaOH and 100 lambda of a 3% solution of hydrogen peroxide for about 12 hours. When milligram amounts of steroid are used for the reaction, a visible spontaneous precipitate is formed as soon as the radioactive iodide in alkaline solution and hydrogen peroxide is added. At the end of this reaction time, the precipitate was removed by centrifugation. The trace of non-reacted iodide was washed away from the sediment with water of 0.1 N HCL. The washed precipitate was then dissolved in methanol. Diluted aliqout fractions of the supernatant and sediment were counted for their radioactivity, the percent labelling and the specific activity per millimole is calculated. About 50–76 percent of added Na-$^{125}$I is labelled to estradiol-17 beta by this procedure. Depending on the concentrations of estradiol and $^{125}$I used in the reaction, the specific activity of the labelled estradiol varied from 0.075–0.8 Ci/mM.

Example II

To obtain higher specific activity, the concentration of estradiol-17 beta was decreased to 2.724 microgram (0.01 micromole) and $^{125}$I was increased to 1 mCi and the reaction was run as before in Example I. At the end of the reaction time, the unreacted $^{125}$I-iodide was removed by transferring the reaction mixture to a Bio-Rad Ag 1×8, 200–400 and the labelled steroid was eluted with methanol. The radioactivity of the collected fractions were determined and the specific activity so obtained was calculated. The percentage labelling so obtained was about 70 and the specific activity of this $^{125}$I labelled estradiol was 70 Ci/mM.

Example III—Iodination of Steroid Hormones by Chloramin-T Reaction

As in previous experiments, estradiol-17 beta dissolved in methanol was added to $^{125}$I as sodium iodide in 0.0005 N sodium or potassium hydroxide in 10 lambda volume. A freshly prepared solution of chloramin-T in distilled water (1 mg) was added and spontaneous precipitation of estradiol from the solution takes place. After 5 minutes reaction time, 0.2 ml, 0.1 N HCL or 0.2 ml distilled water was added to precipitate all the steroid from the solution. The sediment was removed by centrifugation and washed with water or 0.1 N HCL to remove the traces of unreacted iodide. The labelled estradiol was dissolved in methanol and aliqout fractions of both supernatant and dissolved sediment are taken for measurement of radioactivity from which the percent labelling is calculated. The percent $^{125}$I labelling of estradiol be chloramin-T procedure was 80–90.

Example IV—Iodination of Other Steroids and Steroid Hormones

A variety of other steroid hormones were labelled both by the hydrogen peroxide and the chloramin-T procedures as described for the iodine labelling of estradiol-17 beta. The percentage labelling of each of these steroid molecules by both these procedures are summarized in Table I.

TABLE I $^{125}$I LABELLING OF STEROID HORMONES

| No. | Steroid | Percent Labelling Hydrogen Peroxide | Percent Labelling Chloramine-T |
|---|---|---|---|
| 1 | Cholesterol | 20 | 6.2 |
| 2 | Δ$^5$-Pregnenolone | 18 | 14.9 |
| 3 | Progesterone | 39–65 | 39.0 |
| 4 | 17-alpha Hydroxypregnenolone | 11 | 36.31 |
| 5 | 17-alpha Hydroxyprogesterone | 22 | 11.5 |
| 6 | Dehydroepiandrosterone | 10 | 21.0 |
| 7 | Androstenedione | 18 | 52.0 |
| 8 | Testosterone | 18 | — |
| 9 | Estrone | 47.5 | 85.5 |
| 10 | Estradiol 17-B | 46–80 | 95.0 |
| 11 | Estriol | 47 | 48.0 |
| 12 | Espiestriol | 32 | 59.5 |
| 13 | 20-B Hydroxy Δ$^4$-Pregnane-3-one | 19 | 21.0 |
| 14 | 5B Pregnan-3 alpha-20-alpha-diol | 31.3 | 21.0 |
| 15 | Androsterone | 24.2 | 26.0 |
| 16 | Etiocholanolone | 10.3 | 12.0 |
| 17 | Adrenosterone | 38.9 | 62.0 |
| 18 | Corticosterone | 10.8 | 16.0 |
| 19 | Cortisone | 20.5 | 16.0 |
| 20 | Deoxycorticosterone | 68.8 | 50.9 |
| 21 | Dexamethazone | 19.3 | 46.0 |
| 22 | Hydrocortisone | 29.7 | 7.0 |

It is to be observed from the results shown in Table I that the steroids numbered 3, 4, 7, 9, 10, 11, 12, 14, 17, 20 and 21 were labelled with $^{125}$I to the extent of more than 30% by the use of either hydrogen peroxide or chloramine-T during the reaction.

Example V

Attempts to react Na$^{125}$I directly with a steroid were unsuccessful. As described before, 100 mM estradiol-17 beta dissolved in 100 lambda methanol was added to 10 microcurie $^{125}$I as sodium iodide in 0.0005 N potassium hydroxide in 10 lambda volume. No hydrogen peroxide or Chloramine-T was added to the reaction mixture. It was allowed to react at room temperature for 12 hours. At the end of the reaction time, the precipitate was removed by centrifugation and washed with water. The percent labelling is calculated as described before, and in the absence of either H$_2$O$_2$ or Chloramine-T, it is found to be as 9.5; whereas, in the presence of H$_2$O$_2$ or Chloramine-T the percent labelling is about 70–90.

Additional Tests on the Purity of the Iodinated Steroid Hormones

The labelled steroid hormones are separated from the non-reacted iodide either by precipitation and repeated washings or by chromatographic procedures as described before. In addition, they are subjected to the following tests:

1. Thin layer Chromatogram (TLC)—Thin layer chromatogram of the iodinated steroid is run on silica gel using the solvents ethanol, methanol, and ethylacetate in a 94:5:1 ratio and after 1 hour and 40 minutes run, the distribution of radioactivity observed for $^{125}$I labelled estrogen as shown in FIG. 1.

2. Immunological Specificity of Directly Iodinated Estradiol-17 Beta:

Radioimmunoassay procedures are used for the testings of the antigenic specificity of the $^{125}$I labelled estradiol-17 beta.

A. The effect of serial dilutions of estradiol antiserum in it's binding of fixed amount of $^{125}I$ labelled estradiol-17 beta (specific activity 0.8 Ci/mM).

Figure 2:
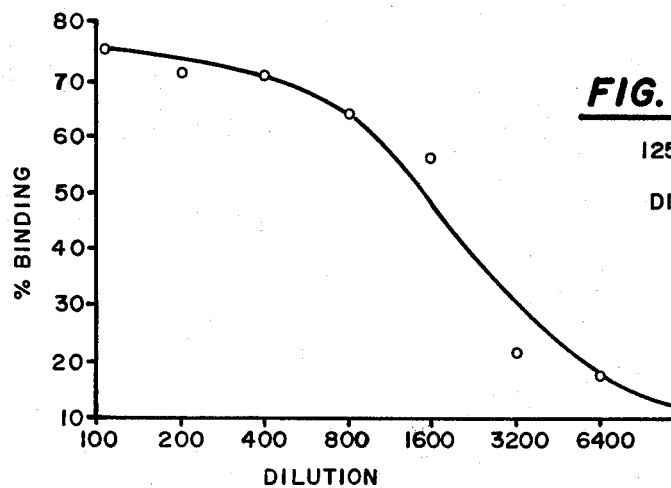
FIG. 2 is a graphical representation of the serial dilutions of an antiserum against estradiol-17 beta wherein the abscissa is the dilution and the ordinate is the % binding.

Serial dilutions of an antiserum against estradiol-17 beta starting from 1:100 to 1:51,200 were made and the percentage binding of about 20 ng $^{125}I$ labelled estradiol-17 beta was determined. The unbound $^{125}I$ estradiol was removed by charcoal adsorption. As shown in FIG. 2, at a lower antiserum dilution of 1:100, the percent bound $^{125}I$ estradiol-17 beta is 75.3. And, as the concentration of antiserum is decreased (dilution increased), a proportionate decrease in antiserum-bound $^{125}I$ estradiol is readily observed.

B. The Radioimmunoassay

Figure 3:
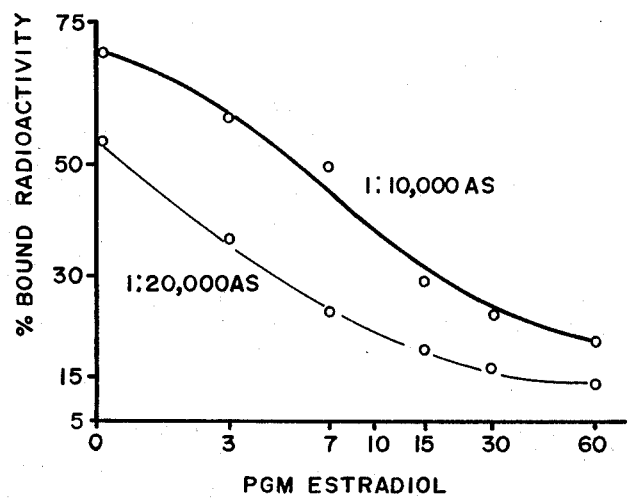
FIG. 3 is a graphical representation of a radioimmunoassay of $^{125}I$-estradiol with unlabelled estradiol wherein the abscissa is the PGM of non-radioactive estradiol and the ordinate is % bound radioactivity with two curves being shown at different dilutions.

The procedure of this assay are identical as described by the instant inventor and authors C. P. Perlia, S. G. Economou, and H. Sky-Peck in Journal of Surgical Onocology, 7:467–477(1975), except for the following modification. To 0.1 ml antiserum 1:10,000 or 1:20,000 dilution and $^{125}I$ estradiol-17 beta (70 Ci/mM), increments of nonradioactive estradiol was added. After incubation, the unbound hormone was removed by charcoal adsorption. As shown in FIG. 3, as the concentration of unlabelled estradiol increases, the percent bound $^{125}I$ estradiol decreases because of the competition for the available binding sites at the antiserum. In comparison with the standard curves obtained for radioimmunoassay of estrogen using $^{3}H$ labelled estradiol, this $^{125}I$ labelled estradiol gave higher sensitivity. This indicates the higher specific activity obtained by the procedure described here for $^{125}I$ labelling of estrogen.

Binding of Directly Iodinated Estradiol-17 Beta to Estrogen Receptor of Human Breast Cancer Estrogen receptor assay of human breast cancer was carried out by incubating the receptor-containing tumor cytosol with radioactive estrogen alone and in parallel experiments with both radioactive and non-radioactive estrogen. The non-radioactive estrogen acts as a competitive inhibitor of the binding of radioactive estrogen to the estrogen receptor sites. The receptor-bound radioactive estrogen is identified by sucrose gradient analysis by which the receptor-bound radioactivity appears at 8S or 5S regions which is competitively inhibited by a higher dose of non-radioactive estrogen.

Tumor cytosols prepared from human breast cancer containing estrogen receptor were assayed by sucrose gradient analysis using tritium labelled estradiol. They are compared with the receptor binding of $^{125}I$ labelled estradiol. It is found that the binding of $^{125}I$ labelled estradiol to estrogen receptor sites are identical, or even superior as compared to the assay results with $^{3}H$ labelled estradiol-17 beta.

Administration of high energy gamma emitting radiolodine labelled steroid hormones or their precursor substances to to patients may greatly improve the ability to visualize the steroid synthesizing organs and/or tumor sites that may contain specific steroid hormone receptor sites by radioisotopic scanning procedures. In addition, such radiolabelled hormones may be trapped at the receptor sites of the tumor tissue and the high energy gamma ray emitted by the receptor-bound radiolabelled hormones may induce specific cytotoxicity at the tumor sites. Organs without specific receptor sites and therefore without any specific concentration of the radioactive hormones may not be affected by such treatment. This approach may allow a systematic treatment with radiolabelled hormones and therefore destruction of tumor by radiation induced cytotoxicity. It could be mediated by the interaction of radiolabelled hormone and the receptor sites of the tumor tissue. By conventional radiotherapy, only localized treatment is possible.

Since the iodinated steroids produced by the process of this invention retain both the antigenicity and the specific binding characteristics which are identical to the naturally occurring steroid hormones, they are physiologically active substances as hormones and they may be used as estrogenic or progestational agents or as glucocorticoid and as anti-inflammatory substances depending upon the physiological role of the parent steroid hormone used for the iodination process.

Steroid hormone is a material secreted by the ductless or endocrine glands having certain functions and characteristics and also includes those compounds, i.e., synthetic analogues, having the cyclopentanophenanthrene nucleus. All of these compounds are chemically very similar, though a comparatively slight structural change produces in many instances physiologically dissimilar effects which often act on entirely different physiologic systems. In many cases, small structural changes will result in the mere accentuation of certain effects.

Thus the steroid hormones and steroidal synthetics, when classified by their predominant pharmacologic effects that can be used as starting materials for this invention include the adrenal corticosteroids, known as anti-inflammatory, antiallergic and antirheumatic agents; the androgens and anabolic agents; the estrogens; the progestogens and progestins; and the diuretic and antidiuretic agents as well as the acetate, succinate, sodium succinate, diacetate, phenylacitate, propionate, benzoate, depropionate and caproate derivatives thereof.

The radioactive steroid hormones of this invention can be formed by direct reaction with a radioactive alkali metal halide such as sodium iodide-125, potassium iodide-125, sodium iodide-123, sodium iodide-131 and potassium iodide-131. The same procedure can be used to prepare the isotopes $^{123}I$ and $^{130}I$ as may be required in tracing receptor sites in tumor tissue where both antigenic and receptor site specificity is required. For these and other purposes other alkali metal halides wherein the halogen is a radioactive isotope having the prerequisite lifetime, mode of decay, decay energy, particle energy and intensity for proper detection and use in such studies can be used. Since the selection of the particular isotope is a matter well known in the art, no further explanation is deemed necessary for purposes of this invention. The process of the invention can also be applied to the use of non-radioactive alkali metal halides to prepare halogenated steroid hormones for selected uses.

What is claimed is:

1. A halogenated steroid hormone suitable for invivo biological studies and treatment prepared by the reaction of a steroid hormone with an alkali metal halide in the presence of an agent selected from the group consisting of hydrogen peroxide and Chloramine-T at ambient temperature.

2. A halogenated steroid hormone in accordance with claim 1 in which the agent is hydrogen peroxide.

3. A halogenated steroid hormone in accordance with claim 1 in which the agent is chloramine-T.

4. Radioactive halogenated steroid hormones for radioimmunoassays and radio-receptor assays prepared by the reaction of the hormone with an alkali metal halide containing radioactive halogen in the presence of an agent selected from the group consisting of hydrogen peroxide and chloramin-T at ambient temperature.

5. Radioactive halogenated steroid hormones in accordance with claim 4 in which the agent is hydrogen peroxide.

6. Radioactive halogenated steroid hormones in accordance with claim 4 in which the agent is chloramin-T.

7. Radioactive halogenated steroid hormones in accordance with claim 4 wherein the radioactive halogen is selected from the group of iodine-123, iodine-125 iodine-130 and iodine-131.

8. A halogenated steroid hormone suitable for invivo biological studies and treatment prepared by the reaction of a steroid hormone with an alkali metal halide in the presence of hydrogen peroxide at ambient temperature.

9. Radioactive halogenated steroid hormones for radioimmunoassays and radio-receptor assays prepared by the reaction of the hormone with an alkali metal halide containing radioactive halogen in the presence of hydrogen peroxide at ambient temperature.

10. The method of preparing high specific radioactive halogenated steroid hormones which comprises:
reacting a steroid hormone with an alkali metal halide containing radioactive halogen in the presence of an alkaline solution of an agent selected from the group consisting of hydrogen peroxide and chloramine-T at ambient temperature; and
separating the radioactive halogenated steroid hormone.

11. The method in accordance with claim 10 in which said steroid hormone is selected from the group consisting of cholesterol, pregnenolone, progesterone, 17-alpha hydroxypregnenolone, 17-alpha hydroxyprogesterone, dehydroepiandrosterone, androstenedione, testosterone, estrone, estradiol 17-B, estriol, epiestriol, 20-B hydroxy pregnane-3-one, 5B pregnan-3 alpha-20-alpha-diol, androsterone, etiocholanolone, adrenosterone, corticosterone, cortisone, deoxycorticosterone, dexamethazone and hydrocortisone.

12. The method in accordance with claim 10 in which said agent is hydrogen peroxide.

13. The method in accordance with claim 10 in which said agent is chloramine-T.

14. The method in accordance with claim 10 in which:
milligram quantities of said steroid hormone are used whereby a spontaneous precipitate is formed.

15. The method in accordance with claim 11 in which said steroid hormone is estradiol-17 beta and the specific activity of the labelled radioactive product is at least about 70 Ci/mM and characterized by increased assay sensitivity.

16. The method of preparing halogenated steroid hormones which comprises:
reacting a steroid hormone with an alkali metal halide in the presence of an alkaline solution of an agent selected from the group consisting of hydrogen peroxide and chloramine-T at ambient temperature; and
separating the halogenated steroid hormone.

* * * * *